(12) United States Patent
Arata et al.

(10) Patent No.: US 9,101,394 B2
(45) Date of Patent: Aug. 11, 2015

(54) IMPLANT PLANNING USING CAPTURED JOINT MOTION INFORMATION

(75) Inventors: Louis Arata, Mentor, OH (US); Alon Mozes, Miami Beach, FL (US); Jason Otto, Plantation, FL (US); Robert Van Vorhis, Davis, CA (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 1429 days.

(21) Appl. No.: 11/963,547

(22) Filed: Dec. 21, 2007

(65) Prior Publication Data

US 2008/0262812 A1    Oct. 23, 2008

Related U.S. Application Data

(60) Provisional application No. 60/925,269, filed on Apr. 19, 2007.

(51) Int. Cl.
*A61B 19/00* (2006.01)

(52) U.S. Cl.
CPC ............. *A61B 19/5244* (2013.01); *A61B 19/52* (2013.01); *A61B 19/50* (2013.01); *A61B 2019/501* (2013.01); *A61B 2019/502* (2013.01); *A61B 2019/504* (2013.01); *A61B 2019/505* (2013.01); *A61B 2019/508* (2013.01); *A61B 2019/5255* (2013.01); *A61B 2019/562* (2013.01)

(58) Field of Classification Search
CPC ............. A61B 19/50; A61B 2019/502; A61B 2019/505; A61B 2019/507; A61B 2019/508; G06F 19/3437; G06T 7/0028

USPC .................................................. 600/587, 595
See application file for complete search history.

(56) References Cited

U.S. PATENT DOCUMENTS

| | | | |
|---|---|---|---|
| 5,086,401 A | 2/1992 | Glassman et al. | 395/94 |
| 5,299,288 A | 3/1994 | Glassman et al. | 393/80 |

(Continued)

FOREIGN PATENT DOCUMENTS

| | | |
|---|---|---|
| DE | 100 31 887 A1 | 1/2002 |
| WO | WO 02/061688 A2 | 8/2002 |

(Continued)

OTHER PUBLICATIONS

O'Driscoll, Shawn W. et al. *"Arthroscopy." Reconstructive Surgery of the Joints.* Ed. Bernard F. Money, M.D. New York: Churchill Livingstone, 1996. 587-608.

(Continued)

*Primary Examiner* — Sean Dougherty
*Assistant Examiner* — Michael C Stout
(74) *Attorney, Agent, or Firm* — Foley & Lardner LLP

(57) ABSTRACT

The description relates to surgical computer systems, including computer program products, and methods for implant planning using captured joint motion information. Data is captured representative of a range of motion of a joint associated with a particular individual, where the joint includes a first bone and a second bone. The first bone of the joint is represented and a first implant model is associated with the representation of the first bone. Based on the captured data, a relationship is determined between the first implant model and a representation of the second bone through at least a portion of the range of motion of the joint. Information is displayed representative of the determined relationship.

23 Claims, 15 Drawing Sheets

(56) References Cited

U.S. PATENT DOCUMENTS

| | | | |
|---|---|---|---|
| 5,408,409 A | 4/1995 | Glassman et al. | 346/413.13 |
| 5,871,018 A | 2/1999 | Delp et al. | |
| 5,880,976 A | 3/1999 | DiGioia, III et al. | 364/578 |
| 5,995,738 A | 11/1999 | DiGioia, III et al. | 395/500.32 |
| 6,002,859 A * | 12/1999 | DiGioia et al. | 703/11 |
| 6,205,411 B1 | 3/2001 | DiGioia, III et al. | 703/11 |
| 6,533,737 B1 | 3/2003 | Brosseau et al. | 60/595 |
| 7,035,716 B2 | 4/2006 | Harris et al. | 700/245 |
| 7,239,908 B1 | 7/2007 | Alexander et al. | |
| 7,387,644 B2 | 6/2008 | Beynnon et al. | |
| 7,981,158 B2 | 7/2011 | Fitz et al. | |
| 8,369,926 B2 * | 2/2013 | Lang et al. | 600/407 |
| 2003/0184297 A1 * | 10/2003 | Jakab | 324/318 |
| 2004/0009459 A1 | 1/2004 | Anderson et al. | |
| 2004/0087869 A1 | 5/2004 | Treppo et al. | |
| 2005/0182320 A1 * | 8/2005 | Stifter et al. | 600/429 |
| 2005/0251065 A1 | 11/2005 | Henning et al. | |
| 2005/0251148 A1 * | 11/2005 | Friedrich et al. | 606/88 |
| 2006/0004284 A1 * | 1/2006 | Grunschlager et al. | 600/416 |
| 2006/0015030 A1 | 1/2006 | Poulin et al. | |
| 2006/0095047 A1 | 5/2006 | de la Barrera | |
| 2006/0142657 A1 * | 6/2006 | Quaid et al. | 600/424 |
| 2006/0161051 A1 | 7/2006 | Terrill-Grisoni et al. | |
| 2006/0275736 A1 | 12/2006 | Wen et al. | |
| 2007/0015995 A1 | 1/2007 | Lang et al. | |
| 2007/0066917 A1 * | 3/2007 | Hodorek et al. | 600/595 |
| 2007/0198022 A1 | 8/2007 | Lang et al. | |
| 2007/0219561 A1 * | 9/2007 | Lavallee et al. | 606/90 |
| 2007/0219639 A1 | 9/2007 | Otto et al. | |
| 2008/0004633 A1 | 1/2008 | Arata et al. | |
| 2008/0058945 A1 | 3/2008 | Hajaj et al. | |
| 2008/0177203 A1 | 7/2008 | von Jako | |
| 2008/0208081 A1 | 8/2008 | Murphy et al. | |
| 2008/0243127 A1 | 10/2008 | Lang et al. | |
| 2008/0262812 A1 | 10/2008 | Arata et al. | |
| 2008/0287962 A1 | 11/2008 | Dick et al. | |
| 2008/0312663 A1 | 12/2008 | Haimerl et al. | |
| 2009/0012532 A1 | 1/2009 | Quaid et al. | |
| 2009/0043556 A1 | 2/2009 | Axelson et al. | |
| 2009/0074252 A1 | 3/2009 | Dariush et al. | |
| 2009/0209884 A1 | 8/2009 | Van Vorhis et al. | |
| 2009/0240169 A1 | 9/2009 | Warkentine et al. | |
| 2009/0254093 A1 | 10/2009 | White et al. | |
| 2009/0270868 A1 | 10/2009 | Park et al. | |
| 2009/0291417 A1 | 11/2009 | Rubbert et al. | |
| 2010/0049195 A1 | 2/2010 | Park et al. | |
| 2010/0076563 A1 | 3/2010 | Otto et al. | |
| 2010/0086186 A1 | 4/2010 | Zug et al. | |
| 2010/0137882 A1 | 6/2010 | Quaid, III | |
| 2010/0153076 A1 | 6/2010 | Bellettre et al. | |
| 2011/0029116 A1 | 2/2011 | Jordan et al. | |

FOREIGN PATENT DOCUMENTS

| WO | 2006/078236 | 7/2006 |
|---|---|---|
| WO | WO-2010/068212 | 6/2010 |
| WO | WO-2010/068213 | 6/2010 |

OTHER PUBLICATIONS

U.S. Appl. No. 12/333,119, filed Dec. 11, 2008, Bellettre et al.
International Search Report and Written Opinion for PCT Application No. PCT/US2008/086461, mailed Sep. 4, 2009, 9 pages.
International Search Report and Written Opinion for PCT Application No. PCT/US2008/086462, mailed Aug. 27, 2009, 12 pages.

* cited by examiner

US 9,101,394 B2

IMPLANT PLANNING USING CAPTURED JOINT MOTION INFORMATION

CROSS REFERENCE TO RELATED APPLICATIONS

The present application claims priority to U.S. Provisional Patent Application Ser. No. 60/925,269, filed on Apr. 19, 2007, which is hereby incorporated by reference herein in its entirety.

BACKGROUND OF THE INVENTION

1. Field of the Invention

The invention relates to surgical computer systems, including computer program products, and methods for implant planning using captured joint motion information.

2. Description of Related Art

Orthopedic joint replacement surgery may involve arthroplasty of a knee, hip, or other joint (e.g., shoulder, elbow, wrist, ankle, fingers, etc.). For example, traditional total knee arthroplasty involves a long incision, typically in a range of about 6 to 12 inches, to expose the joint for bone preparation and implantation of implant components. The invasive nature of the incision results in a lengthy recovery time for the patient. Minimally invasive surgery (MIS) reduces the incision length for a total knee replacement surgery to a range of about 4 to 6 inches. However, the smaller incision size reduces a surgeon's ability to view and access the anatomy of a joint. Consequently, the complexity of assessing proper implant position and reshaping bone increases, and accurate placement of implants may be more difficult. Inaccurate positioning of implants may lead to reduced range of motion of a joint, impingement, and subsequent dislocation. For example, one problem with total hip replacement is dislocation of a femoral implant from an acetabular cup implant caused, for example, by impingement, which in turn may be caused by inaccurate positioning of the acetabular cup implant within a pelvis.

Another drawback of both MIS and traditional orthopedic surgical approaches is that such approaches do not enhance the surgeon's inherent surgical skill in a cooperative manner. For example, some conventional techniques for joint replacement include autonomous robotic systems to aid the surgeon. Such systems, however, typically serve primarily to enhance bone machining by performing autonomous cutting with a high speed burr or by moving a drill guide into place and holding the position of the drill guide while the surgeon inserts cutting tools through the guide. Although such systems enable precise bone resections for improved implant fit and placement, they act autonomously (rather than cooperatively with the surgeon) and thus require the surgeon to cede a degree of control to the robot.

Other conventional robotic systems include robots that cooperatively interact with the surgeon. One drawback of conventional interactive robotic systems is that such systems lack the ability to adapt surgical planning and navigation in real-time to a dynamic intraoperative environment. For example, U.S. Pat. No. 7,035,716, which is hereby incorporated by reference herein in its entirety, discloses an interactive robotic system programmed with a three-dimensional virtual region of constraint that is registered to a patient. The interactive robotic system requires a relevant anatomy to be rigidly restrained and the robotic system to be fixed in a gross position and thus lacks real-time adaptability to the intraoperative scene. Moreover, a three degree of freedom arm configuration and the requirement that the surgeon manipulate the arm using a force handle results in limited flexibility and dexterity, making the robotic system unsuitable for certain MIS applications such as intraoperative implant planning.

An important aspect of implant planning concerns variations in individual anatomies. As a result of anatomical variation, there is no single implant design or orientation of implant components that provides an optimal solution for all patients. Some conventional intraoperative positioning devices for implant planning used by surgeons to align an acetabular hip implant with respect to the sagittal and coronal planes of a patient assume that the patient's pelvis and trunk are aligned in a known orientation and do not take into account individual variations in the patient's anatomy or pelvic position on the operating room table. B. F. Morrey, editor, "Reconstructive Surgery of the Joints", chapter Joint Replacement Arthroplasty, pages 605-608, Churchill Livingston, 1996. Implant planning based on such types of conventional devices can lead to a large discrepancy between desired and actual implant placement, possibly resulting in reduced range of motion of a joint, impingement, and dislocation.

Several attempts have been made to more precisely prepare the acetabular region for hip implants. U.S. Pat. Nos. 5,880,976; 5,995,738; 6,002,859; and 6,205,411, issued to DiGioia et al. and hereby incorporated by reference herein in their entirety, are directed to biomechanical simulations of the movement of a joint containing implant models performed under a number of test positions, including a desired range of motion of the joint. Although the DiGioia patents describe a system that may offer the potential for increased accuracy and consistency in the preparation of the acetabular region to receive implants, a shortcoming of the system is that movement of the joint is only simulated. The accuracy and consistency of the actual implant results depend on how closely the simulated motion of the joint corresponds to the actual motion of the joint. Moreover, simulated joint movement does not account for actual motion of a joint with individual variations.

U.S. Pat. Nos. 5,086,401; 5,299,288; and 5,408,409, issued to Glassman et al. and hereby incorporated by reference herein in their entirety, disclose an image directed surgical robotic system for broaching a femur to accept a femoral implant using a robotic cutter system. In the system, the coordinates and structure of a joint model are determined during an intraoperative planning phase where a surgeon manually interactively selects and positions an implant relative to images of the joint into which the implant is to be implanted. Although the Glassman patents describe a system that may offer the potential for increased accuracy and consistency in the preparation of bones to receive implants, the system lacks real-time adaptability to the intraoperative scene and consistent, predictable results regardless of surgical skill level because the surgeon manually has to interact and analyze relative discrete positions of implants in a joint rather than analyzing the implants during continuous motion of the joint.

In view of the foregoing, a need exists for surgical methods and devices which can overcome the aforementioned problems so as to enable intraoperative implant planning for accurate placement and implantation of joint implants providing an improved range of motion of a joint; consistent, predictable operative results regardless of surgical skill level; sparing healthy bone in minimally invasive surgery; and reducing the need for replacement and revision surgery.

SUMMARY OF THE INVENTION

In one aspect, there is a surgical planning method. The method includes capturing data representative of a range of motion of a joint associated with a particular individual, the joint comprising a first bone and a second bone, representing the first bone of the joint, and associating a first implant model with the representation of the first bone. The method also includes, based on the captured data, determining a relationship between the first implant model and a representation of the second bone through at least a portion of the range of motion of the joint and displaying information representative of the determined relationship.

In another aspect, there is a surgical planning method. The method includes capturing data representative of a range of motion of a joint associated with a particular individual, the joint comprising a first bone and a second bone, creating a representation of the joint comprising a representation of the first bone and a representation of the second bone, and superimposing a first implant model on the representation of the first bone and a second implant model on the representation of the second bone. The method also includes, based on the captured data, displaying the representations of the first and second bones as the representation of the joint moves through the range of motion to determine a relationship between the first and second implant models and adjusting a size, a shape, a position, or any combination thereof of the first implant model, the second implant model, or both based on the determined relationship.

In another aspect, there is a surgical computing system that includes a computer. The computer is configured to capture data representative of a range of motion of a joint associated with a particular individual, represent a first bone of the joint, and associate a first implant model with the representation of the first bone. The computer is also configured to, based on the captured data, determine a relationship between the first implant model and a representation of a second bone of the joint through at least a portion of the range of motion of the joint.

Any of the above aspects can include one or more of the following features. A user can be enabled to change a position of the first implant model. The first implant model can be associated with the representation of the first bone based on the changed position and, based on the captured data, a relationship between the first implant model at its changed position and a representation of the second bone can be determined through at least a portion of the range of motion of the joint. The representation of the second bone can include a representation of a surface of the second bone, a second implant model associated with the representation of the second bone, or both.

A position of the first bone and a position of the second bone can be captured and the positions can be record as the joint moves through the range of motion. The position of the first implant model can be represented relative to a position of the representation of the second bone and the positions at any selected angle can be compared within the range of motion of the joint, inclusive. A position of the first bone and a position of the second bone can be captured and the positions can be record as the joint moves through the range of motion. The position of the first implant model can be represented relative to a position of the representation of the second implant model and the positions at any selected angle can be compared within the range of motion of the joint, inclusive An overlap, a gap, or both can be identified between the first implant model and the representation of the second bone or between the first implant model and a second implant model associated with the second bone at one or more angles within the range of motion of the joint, inclusive. A calculated measurement of the overlap, the gap, or both at any selected angle or at a plurality of angles within the range of motion of the joint, inclusive, can be displayed. A graph representing calculated measurements of the overlap, the gap, or both at a plurality of angles within the range of motion of the joint, inclusive, can be displayed. The overlap, the gap, or both can be displayed in a representation of at least a portion of the joint at one or more angles within the range of motion of the joint, inclusive.

At least one point on a surface of the first implant model can be mapped at a plurality of angles within the range of motion of the joint, inclusive and at least one of the mapped points can be aligned with the representation of the second bone. A second implant model can be associated with the representation of the second bone based on at least one of the mapped points. Data representative of a manipulation of the joint can be captured to achieve a desired internal/external angle, varus/valgus angle, flexion angle, or any combination thereof. A user can be enabled to manipulate placement of at least one implant model corresponding to at least a portion of an actual implant so that the determined relationship through at least a portion of the range of motion of the joint allows the desired internal/external angle, varus/valgus angle, flexion angle, or any combination thereof.

The surgical computing system can include a tracking system in communication with the computer, the tracking system including a detection device and one or more trackers which each include a coupling means to couple the tracker to a bone of the joint. The surgical computing system can include a display in communication with the computer and configured to display information received from the computer that is representative of the determined relationship. The computer of the surgical computing system can be further configured to generate a user interface that enables a user to select an angle at which the determined relationship is calculated, displayed, or both. The computer of the surgical computing system can be further configured to generate a user interface that enables a user to change a position of the first implant model.

There can also be a computer program product, tangibly embodied in an information carrier, where the computer program product includes instructions being operable to cause a data processing apparatus to perform any of the methods described above.

BRIEF DESCRIPTION OF THE DRAWINGS

The accompanying drawings, which are incorporated in and constitute a part of this specification, illustrate embodiments of the invention and together with the description serve to explain principles of the invention.

DETAILED DESCRIPTION OF PREFERRED EMBODIMENTS

Figure 1A:
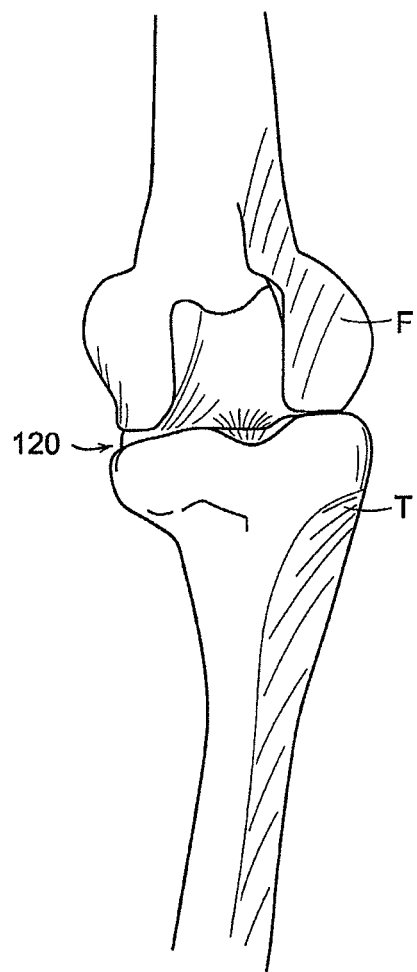
FIG. 1(a) is a front perspective view of a femur and a tibia of a knee joint at a flexion angle of 0 degrees.

Presently preferred embodiments are illustrated in the drawings. Although this specification refers primarily to unicondylar knee joint replacement surgery, it should be understood that the subject matter described herein is applicable to other joints in the body, such as, for example, a shoulder, elbow, wrist, spine, hip, or ankle and to any other orthopedic and/or musculoskeletal implant, including implants of conventional materials and more exotic implants, such as orthobiologics, drug delivery implants, and cell delivery implants.

Representation of a Joint and Implant Models

FIG. 1(a) shows a front view of a tibia T (e.g., a first bone) and a femur F (e.g., a second bone) of a joint 120 without any implant and with the joint 120 at full extension (i.e., a flexion angle θ of 0 degrees). Position trackers (e.g., such as those shown in FIG. 15 and described in more detail below) that are detectable by a detection device, such as an optical camera, are affixed to the femur F and the tibia T of the joint 120. The detected position of the tibia tracker relative to the femur tracker is captured or recorded in given degree intervals (e.g., 3 degrees) as the joint 120 is moved throughout the normal range of motion of the joint 120 from extension to flexion, or any desired set of anatomical orientation angles (for the knee, flexion or extension, varus or valgus, internal or external rotations). The captured movement of the femur F and the tibia T of the joint 120 is registered, respectively, to images of the femur F and the tibia T (e.g., to segmented CT data of the femur F and the tibia T acquired before the surgery begins and/or to representations or models of the femur F and the tibia T generated, for example, from the segmented CT data). This registration establishes coordinate transformations between the position trackers on the femur F and the tibia T (i.e., the physical space) and the respective images of the femur F and the tibia T (i.e., the image space) so that the position of the physical bones can be correlated to the images of the bones. Segmentation and registration may be accomplished using any known technique, such as the techniques described in U.S. Patent Publication 2006/0142657, published Jun. 29, 2006, which is hereby incorporated by reference herein in its entirety. Similarly, coordinate transformations may be determined using any known technique, such as the techniques described in U.S. patent application Ser. No. 11/750,840, filed May 18, 2007, which is hereby incorporated by reference herein in its entirety.

Figure 1B:
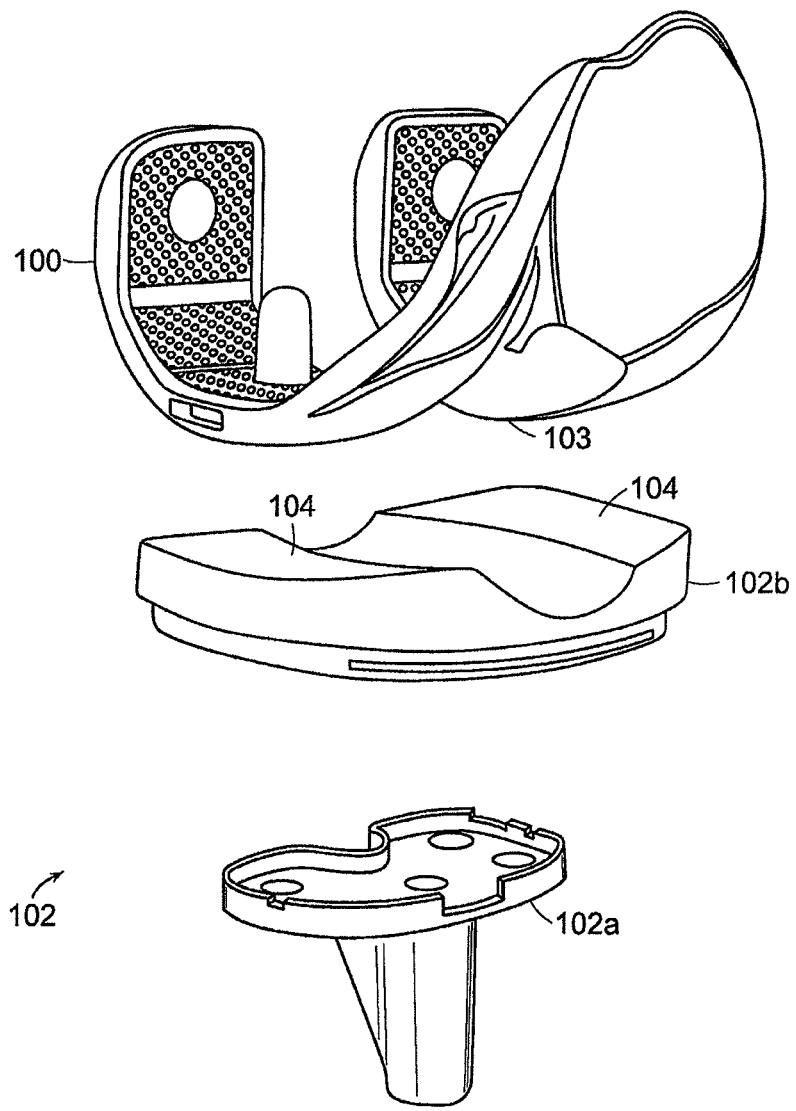
FIG. 1(b) is a perspective view of a conventional total knee arthroplasty system.

FIG. 1(b) shows, and exemplary conventional total knee arthroplasty (TKA) systems typically include, a femoral implant 100 and a tibial implant 102. The femoral implant 100 is typically a single solid component affixed to the femur F. The tibial implant 102 may include a tibial baseplate 102a affixed to the tibia T and a tibial insert 102b which forms the bearing surfaces 104 of the tibial implant 102. In operation, bearing surfaces 103 of the femoral implant 100 articulate against the bearing surfaces 104 of the tibial implant 102 as the knee joint 120 moves through a range of motion.

Figure 1C:
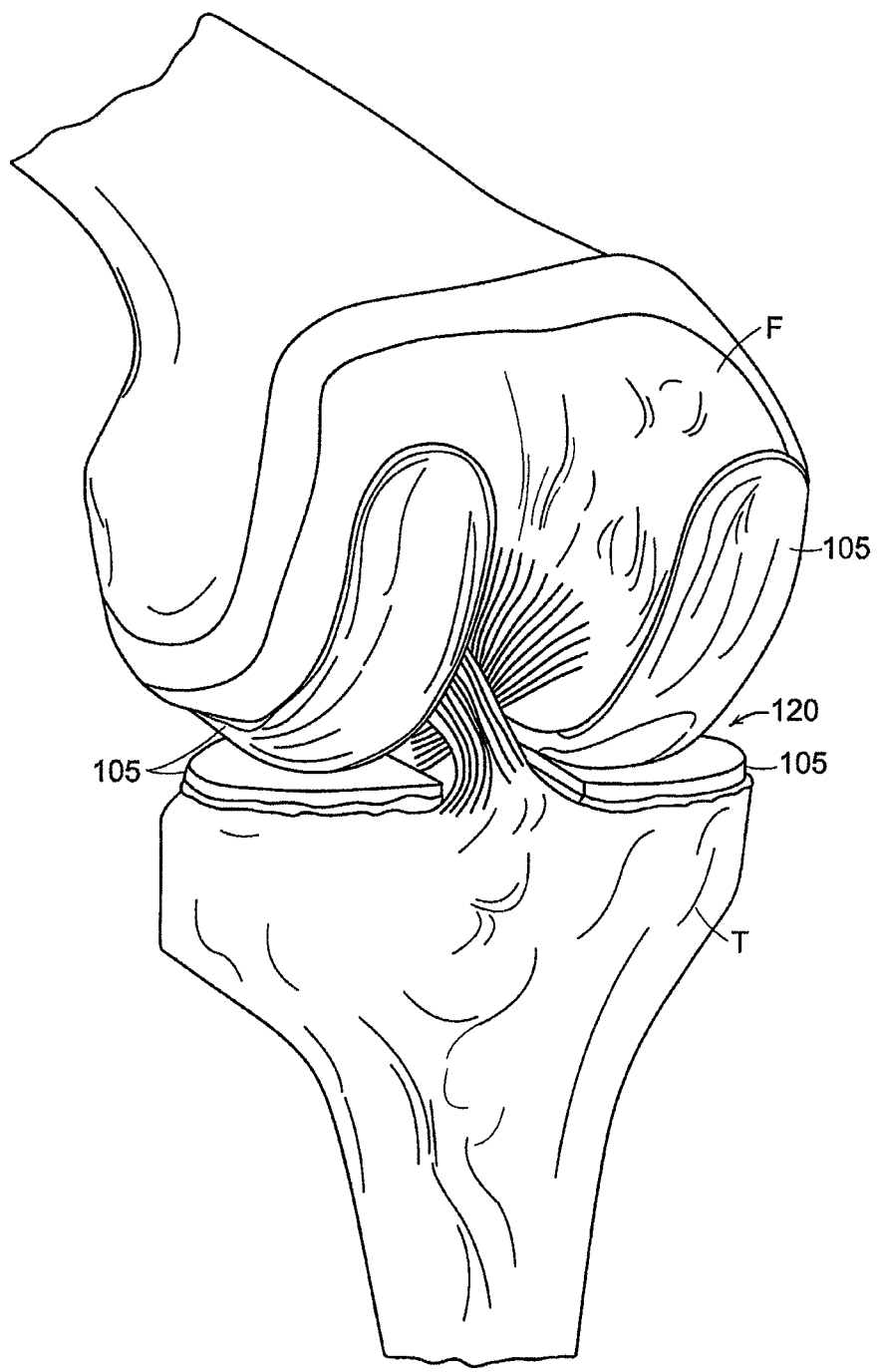
FIG. 1(c) is a perspective view of a conventional bicondylar knee arthroplasty system.
Figure 2:
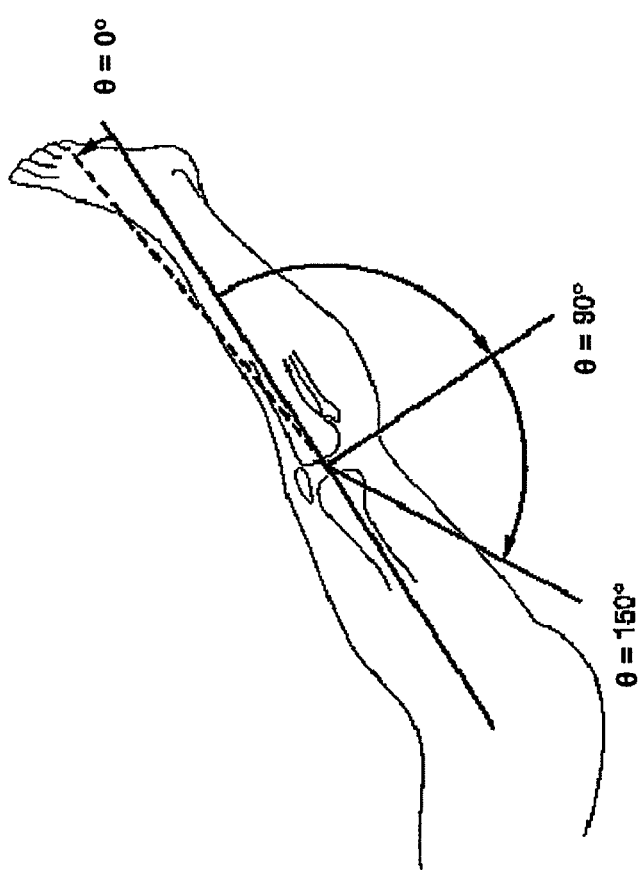
FIG. 2 illustrates a range of motion and a flexion angle of a knee joint.

FIG. 1(c) shows a perspective view of the tibia T and the femur F of the knee joint 120 with multiple unconnected implants 105. The unconnected implants 105 may form a bicondylar implant (as shown in FIG. 1(c)), a unicondylar implant, or a modular segmented implant as described, for example, in U.S. patent application Ser. No. 11/684,514, filed Mar. 9, 2007, and hereby incorporated by reference herein in its entirety. These unconnected implants 105 may require accurate alignment relative to one another to achieve desired joint kinematics and/or to avoid reduced range of joint motion, impingement, and subsequent dislocation. To achieve these objectives, the surgeon can virtually plan implant placement prior to making any bone cuts. Implant planning may be accomplished, for example, as described in the above-referenced U.S. Patent Publication 2006/0142657. According to some embodiments, the femur F and the tibia T of the knee joint 120 with the implants 105 may be virtually represented and their relative positions manipulated and analyzed by performing matrix transformations using the segmented CT data as described below.

Let $T_{tf}$ be the transform from the tibia tracker to the femur tracker at any desired flexion angle. Let $T_{td}$ and $T_{fd}$ be the transforms from the tibia tracker to the tibia CT data and from the femur tracker to the femur CT data, respectively. Then the segmented CT data of the tibia T can be positioned relative to the segmented CT data of the femur F using the matrix composition $T_{td}^{-1} \, T_{tf} \, T_{fd}$, where the superscript "−1" denotes matrix inversion. Similarly, the segmented CT data of the femur F can be positioned relative to the segmented CT data of the tibia T using the matrix composition $T_{fd}^{-1} \, T_{tf}^{-1} \, T_{td}$.

Figure 3:
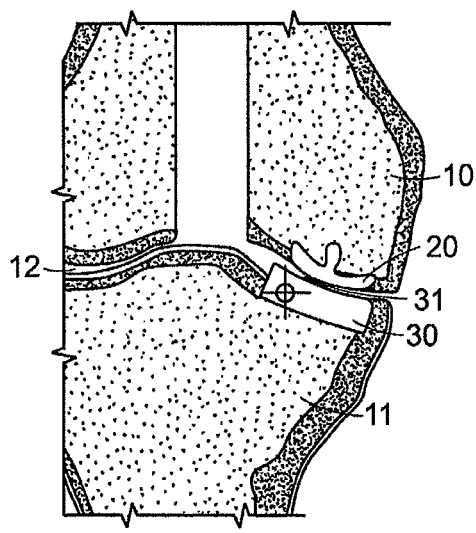
FIG. 3 is a front cross sectional view of an embodiment of a representation of a joint at a flexion angle of 0 degrees.
Figure 4:
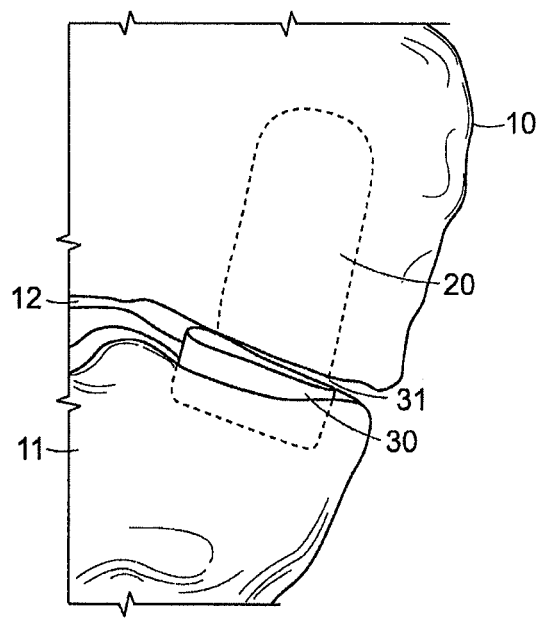
FIG. 4 is a front perspective view of the representation of FIG. 3.

FIG. 3 shows a cross sectional view of a 2D display of a virtual representation 12 of the joint 120 at a flexion angle θ of 0 degrees. Similarly, FIG. 4 shows a 3D display of the virtual representation 12 of the joint 120 at a flexion angle θ of 0 degrees. As shown in FIG. 3, the virtual representation 12 of the joint 120 can include a representation 10 of the femur F and a representation 11 of the tibia T. A tibial implant model 30 (e.g., a first implant model) and a femoral implant model 20 (e.g., a second implant model) can be associated with (i.e., registered to) the representation 11 of the tibia T and the representation 10 of the femur F, respectively. This may be accomplished in any known manner, such as, for example, the implant planning process described in the above-referenced U.S. Patent Publication 2006/0142657. In some embodiments, the representations 10, 11 are graphic models of the femur F and the tibia T generated from the segmented CT data as is well known. To directly compare two implant models at any desired flexion angle let $T_{ifd}$ be the transform from the femoral implant model 20 to the femoral CT data and $T_{itd}$ be the transform from the tibial implant model 30 to the tibial CT data. Then the femoral implant model 20 can be positioned relative to the tibial implant model 30 at any desired flexion angle θ by using the relationship $T_{ifd} T_{fd}^{-1} T_{tf}^{-1} T_{td} T_{itd}^{-1}$.

This registration enables the captured data representing the range of motion of the joint 120 to be "played back" to the user so that the user can visualize the relative motion of the "disarticulated" segmented femur F and tibia T of the CT data with the femoral and tibial implant models 20, 30 superimposed on the representations 10, 11 of the femur F and the tibia T of the joint 120. For example, the actual physical motion of the joint 120 can be visualized by displaying the representation 10 of the femur F and the representation 11 of the tibia T and moving the representations 10, 11 in accordance with how the femur F and the tibia T actually move (i.e., based on the captured range of motion data). When the implant models 20, 30 are superimposed on the representations 10, 11 (e.g., as shown in FIG. 3), the relative position of the implant models 20, 30 can be seen at any selected angle within the range of motion of the joint 120. The user can also determine whether there is a gap (i.e., a space) or an overlap (i.e., an interference) between the implant models 20, 30 at any selected angle within the range of motion of the joint 120. Gap and overlap are discussed further below in connection with FIGS. 5 and 9.

Figure 6:
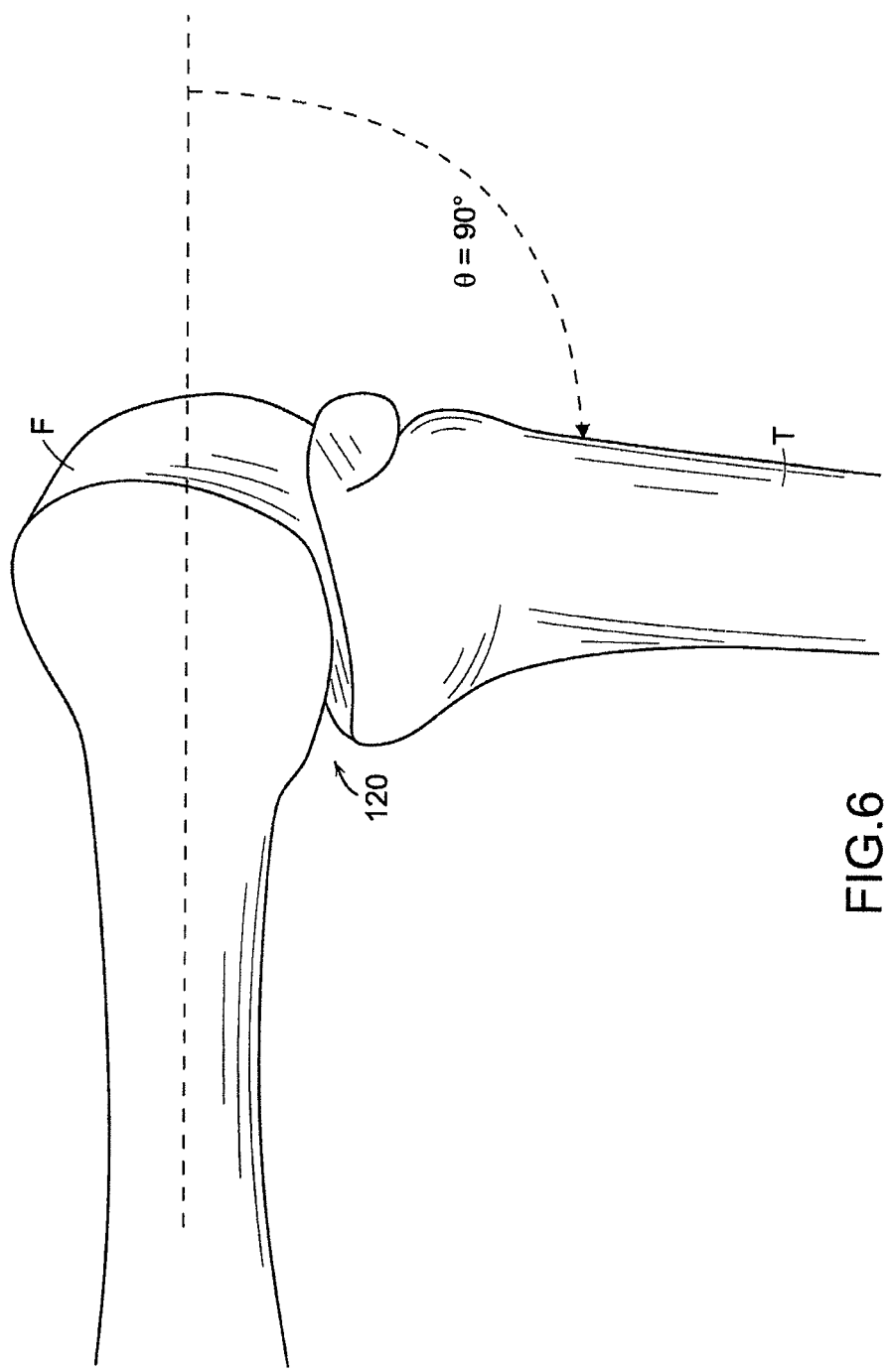
FIG. 6 is a side view of the femur and the tibia of FIG. 1 at a flexion angle of 90 degrees.
Figure 7:
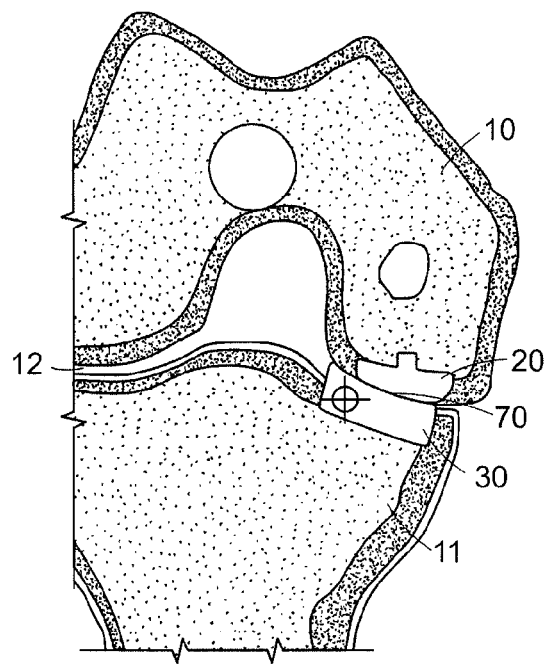
FIG. 7 is a front cross sectional view of an embodiment of a representation of a joint at a flexion angle of 90 degrees.
Figure 8:
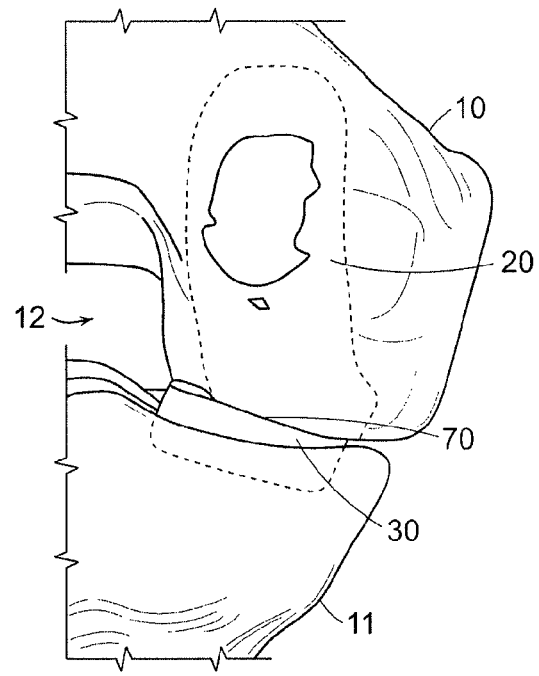
FIG. 8 is a front perspective view of the representation of FIG. 7.

Anatomical axes can be defined in the CT data for the femur F and tibia T of the joint 120. Once this has been done, anatomical angles (e.g., flexion angle, varus/valgus angle, internal/external angle) for any position of the joint 120 can be computed and displayed for any orientation of the captured data representing the range of motion or in "real time" as the joint 120 is manipulated. FIG. 6 shows a side view of the femur F and the tibia T of the joint 120 without any implant at a flexion angle θ of 90 degrees. The amount of gap or overlap between the implant models 20, 30 can be determined for the implant models 20, 30 associated with (e.g., superimposed on) the representations 10, 11 of the femur F and the tibia T at a selected flexion angle θ (e.g., 0 degrees as shown in FIG. 3, 90 degrees as shown in FIG. 6) of the joint 120. This information can be used to plan the placement in the joint 120 of the actual implants that correspond to the implant models 20, 30. For an example, if an overlap 70 is detected between the implant models 20, 30 (as shown in FIGS. 7 and 8), the surgeon may decide to reposition the femoral implant model 20 and/or the tibial implant model 30 to eliminate the overlap 70.

According to some embodiments, one or more implant models may be used. For example, as described above, in one embodiment, both the femoral implant model 20 and the tibial implant model 30 may be used to evaluate relative positions of the two implant models 20, 30. This embodiment may be useful in cases where a patient is having both the femur F and the tibia T resurfaced. In such cases, the implant models 20, 30 can be used to plan placement of the actual femoral and tibial implant components that will be implanted in the femur F and the tibia T of the patient. Alternatively, in another embodiment, only the tibial implant model 30 may be used to evaluate relative positions between the tibial implant model 30 and a surface of the representation 10 of the femur F. The surface of the representation 10 may correspond, for example, to an actual surface of the patient's femur F or to previously installed implant that is now part of the patient's joint 120. This embodiment may be useful in cases where the femur F is not being resurfaced at all or where a previously installed femoral implant is not being replaced or modified. Similarly, in another embodiment, only the femoral implant model 20 may be used to evaluate relative positions of the femoral implant model 20 and a surface of the representation 11 of the tibia T. The surface of the representation 11 may correspond, for example, to an actual surface of the patient's tibia T or to a previously installed implant that is now part of the patient's joint 120. In other embodiments, additional implant models may be included, such as models of the modular segmented components described in U.S. patent application Ser. No. 11/684,514, filed Mar. 9, 2007, and hereby incorporated by reference herein in its entirety.

Overlap and Gap Analysis

As described above, the placement of one implant model relative to another or the placement of an implant model relative to a surface of a bone can be visualized and analyzed throughout the range of motion of the joint 120. For example, the relative placement of the tibial implant model 30 and the femoral implant model 20 can be visualized and evaluated. In one embodiment, when the lowest signed distance between the surface of the femoral implant model 20 and the surface of the tibial implant model 30 is a positive value, a gap 31 is detected between the implant models 20, 30 as shown in FIGS. 3 and 4.

Figure 5:
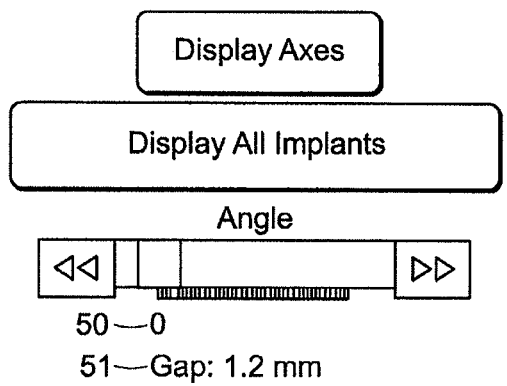
FIG. 5 illustrates an embodiment of a computer display of a gap analysis at a flexion angle of 0 degrees.

FIG. 5 shows an example computer display of a gap analysis of the positions of the implant models 20, 30. In one embodiment, the computer display includes a user input 50 for inputting a selected flexion angle θ and an indicator 51 that shows a value of the gap 31 at the selected flexion angle θ. In the example of FIG. 5, at a flexion angle of 0 degrees, there is a gap 31 of 1.2 mm between the femoral implant model 20 and the tibial implant model 30. Likewise, when the lowest signed distance between the surfaces of the implant models 20, 30 is a negative value, an overlap is detected between the implant models 20, 30.

FIG. 7 shows a front cross sectional view of a 2D display of the representations 10, 11 of the femur F and tibia T. Also shown in FIG. 7 are the implant models 20, 30 associated with the representations 10, 11 of the femur F and the tibia T at a flexion angle θ of 90 degrees.

FIG. 8 shows a front view of a 3D display of the representations 10, 11 of the femur F and the tibia T associated with the representations of the femoral implant model 20 and the tibial implant model 30 at a flexion angle θ of 90 degrees.

Figure 9:
FIG. 9 illustrates an embodiment of a computer display of an overlap analysis at a flexion angle of 90 degrees.

FIG. 9 shows an example of a computer display of an overlap analysis of the positions of the implant models 20, 30 at a flexion angle θ of 90 degrees. In one embodiment, the computer display includes a user input 90 for inputting a selected flexion angle θ and an indicator 91 that shows that the value of the overlap 70 at the selected flexion angle θ. In the example of FIG. 9, at a flexion angle of 90 degrees, there is an overlap of 0.3 mm between the femoral implant model 20 and the tibial implant model 30. Based on the information provided by the virtual analysis shown in FIGS. 5 and 9, when a surgeon is planning the placement of actual implants corresponding to the implant models 20, 30, he can adjust the implant models 20, 30 to achieve the desired relationship between the implant models 20, 30 at any selected angle within the range of motion of the joint. For example, the surgeon may adjust the implant models 20, 30 to ensure that the gap 31 is filled at the flexion angle of 0 degrees and the overlap 70 is removed at the flexion angle of 90 degrees by repositioning the implant models 20, 30 until the surfaces of the implant models 20, 30 just "touch" each other at selected angles within the range of motion of the joint 120.

Figure 9A:
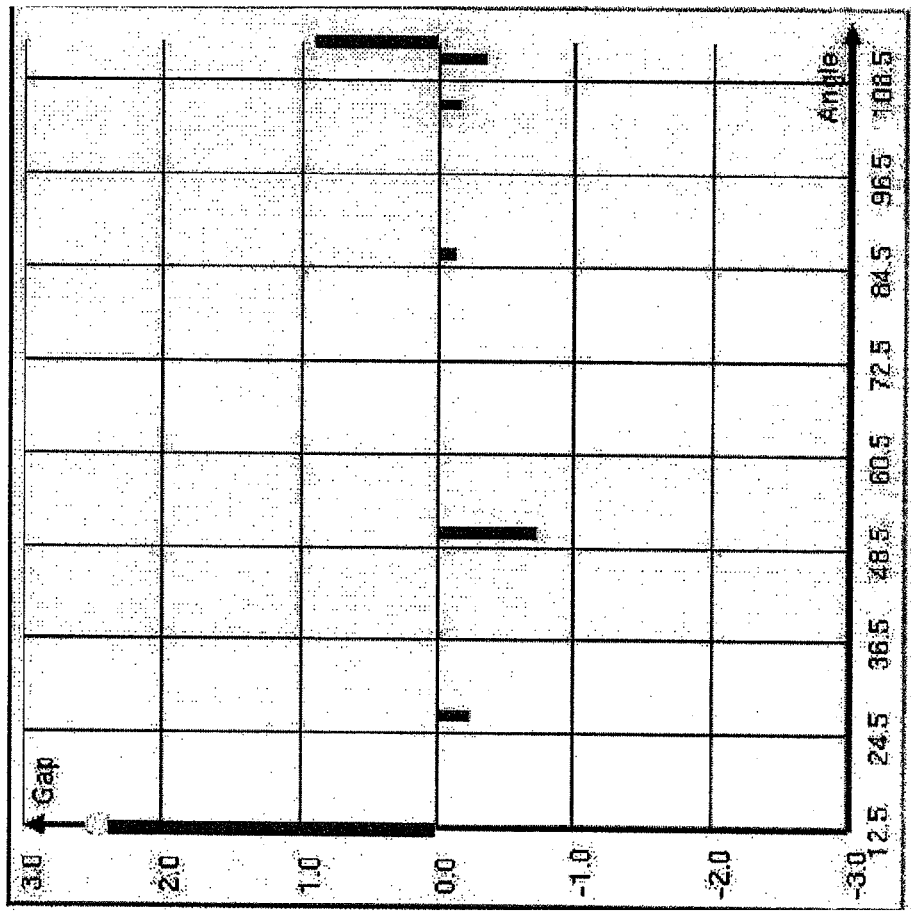
FIG. 9(a) illustrates an embodiment of a computer display of a graph of the gap/overlap analysis over a range flexion angles.

FIG. 9(a) shows another example of a computer display with a graph 600 that graphs the gap/overlap analysis of the positions of the implant models 20, 30 over a range of flexion angles. The horizontal axis of the graph 600 displays the value of the flexion angle. Although the exemplary graph 600 includes angles 12.5 degrees through 108.5 degrees, any range of angles can be displayed. The vertical axis of the graph 600 displays the value of the calculated gap or overlap between two measured points (e.g., the first implant and the second bone, the first implant and the second implant, etc.). In the graph 600, the positive axis represents a gap between the two measured points, with the number representing the distance of the gap, in millimeters. In the graph 600, the negative axis represents an overlap between the two measured points, with the number representing the distance of the overlap, in millimeters. As described herein, the position of the implant (s) can be manipulated through the user interface, so that the surgeon can see the gap/overlap analysis at different implant positions. In such situations, the graph 600 updates as the implant positions are adjusted. With the graph, the user (e.g., the surgeon) can advantageously see all gaps and overlaps over the entire range in one display. This enables the user to slightly modify the position of the implant(s) and receive feedback on the modification over the entire range. The user can then adjust the position to achieve a desired goal (e.g., minimize all gaps and overlaps, minimize center gaps and overlaps at the expense of larger gaps and overlaps at the ends of the range, etc.).

The movement of the femur F and tibia T of the joint 120 can be captured and registered both before and after bone cutting and can be used to compare preoperative and intraoperative ranges of motion of the joint 120 to determine if any over-correction or under-correction has occurred. Accordingly, the surgeon can adjust the plan and continue to cut the bone to adjust for any problems.

Mapped Points Analysis

Figure 11:
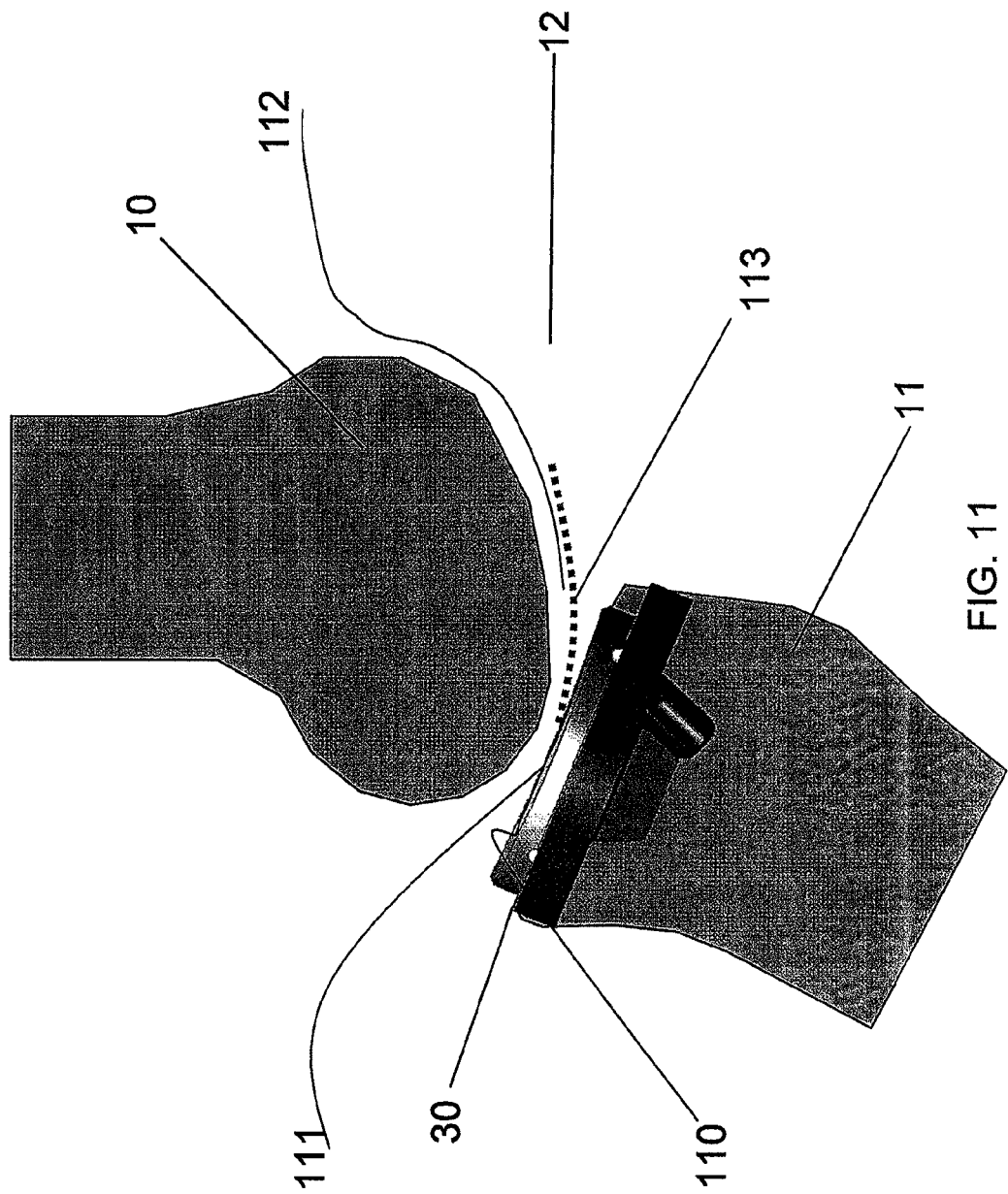
FIG. 11 is a side view of the representation of FIG. 10 at a second flexion angle and showing an embodiment of a point mapping of a first implant model.
Figure 12:
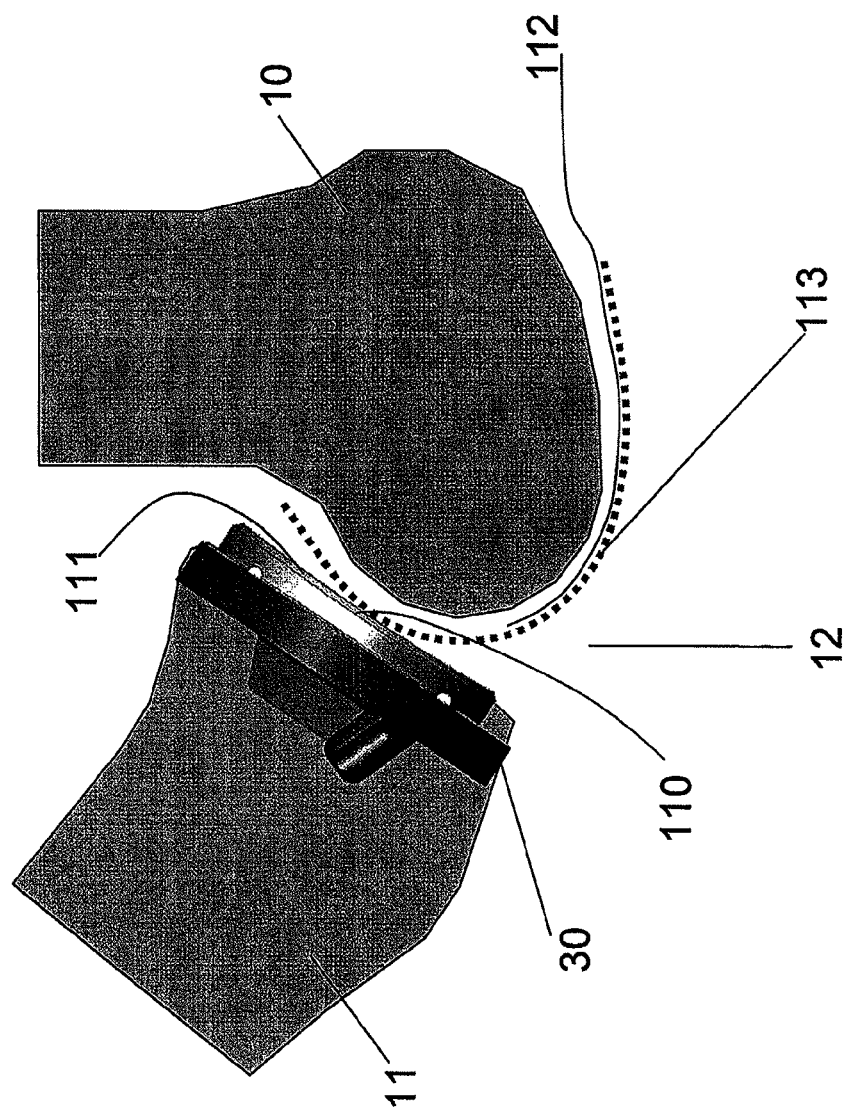
FIG. 12 is a side view of the representation of FIG. 10 at a third flexion angle and showing an embodiment of a point mapping of a first implant model.
Figure 13:
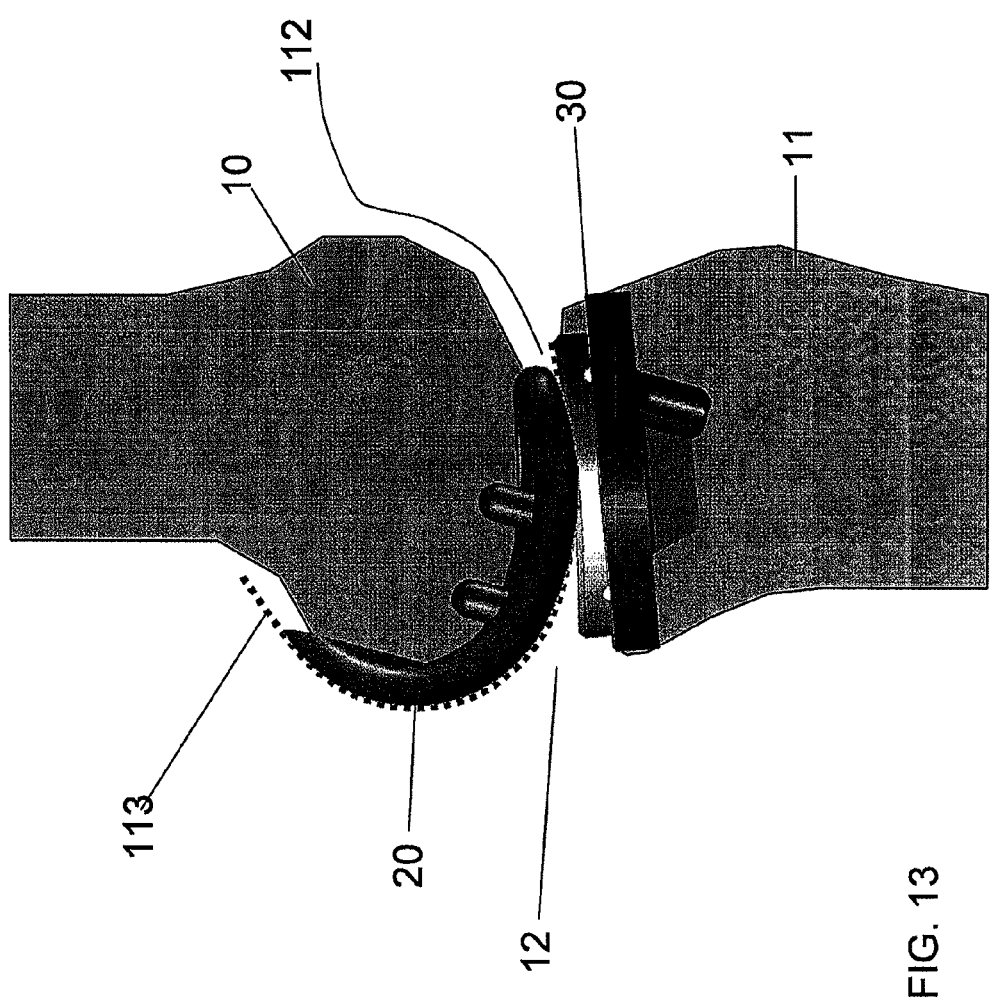
FIG. 13 is a side view of the representation of FIG. 10 showing an embodiment of a point mapping of a first implant model and a second implant model positioned relative to the point mapping.

Referring to FIGS. 11-13, further analysis can be performed by selecting one or more points on the articulating surface of a first implant model (e.g., points near the center, anterior, and posterior of the surface of the tibial implant model 30), mapping these points at multiple angles of joint flexion into the space of an opposite bone (e.g., the representation 10 of the femur F) and/or a second counterpart implant model (e.g., the femoral implant model 20) using the transform relationships described previously, and displaying these mapped points in 3D or projected 2D relative to the opposite bone and/or the second implant model. Mapping may be accomplished, for example, by determining a position of each of the selected points at each of the multiple angles of joint flexion. These "mapped" points can then be used to guide the placement of the second implant model. For example, the second implant model (e.g., the femoral implant model 20) can be positioned so that the articulating surface of the second implant model has a desired relationship to the articulating surface of the first implant model (e.g., the tibial implant model 30) as represented by the mapped points. Similarly, the first implant model (e.g., the tibial implant model 30) can be positioned so that the articulating surface of the first implant model will have a desired relationship to the articulating surface of the opposite bone (e.g., the representation 10 of the femur F). Repositioning the first implant model will update the positions of the mapped points so that the relationship of the second implant model and/or the opposite bone to the first implant model can always be reestablished.

One example of this is to select central, anterior, and posterior points on the surface of a tibial implant model and use these mapped points to align the position and orientation of a femoral implant model as illustrated in FIGS. 11-13.

Figure 10:
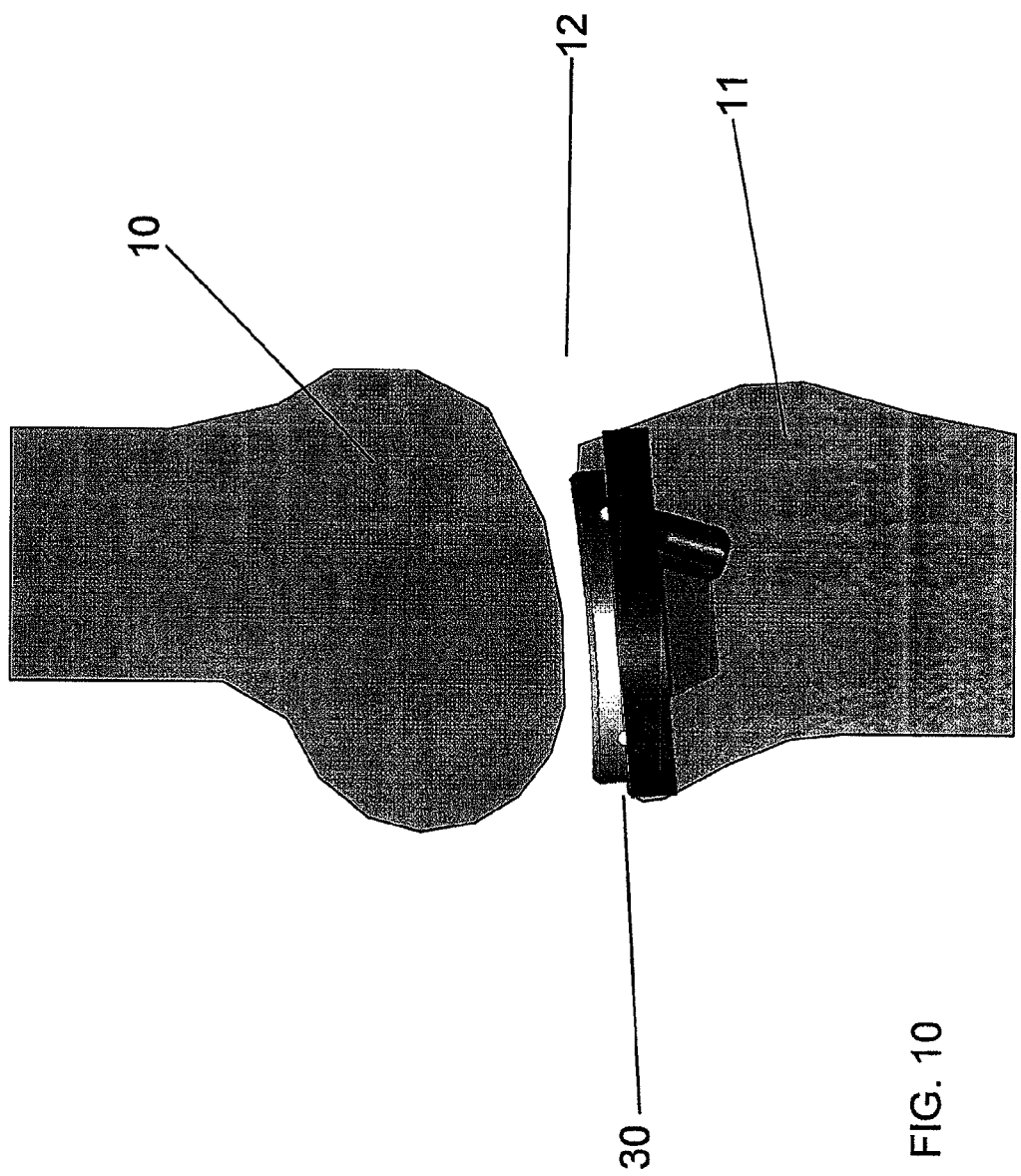
FIG. 10 is a side view of an embodiment of a representation of a joint at a first flexion angle.

For example, FIG. 10 shows a side view of a representation 12 of the joint 120. The representation 12 includes the representations 10, 11 of the femur F and the tibia T, respectively, for the joint 120 at a flexion angle of 0 degrees. A first implant model 30 is associated with (e.g., superimposed on or registered to) the representation 11 of the tibia T. The representations 10, 11 can be used to accomplish point mapping. According to some embodiments, as shown in FIGS. 11 and 12, one or more points 110 of an articulating surface 111 of the first implant model 30 can be mapped to an articular space 112 of the femur F at multiple angles of the range of motion of the joint 120. The mapped points 113 are preferably displayed relative to the representations 10, 11. FIG. 11 shows the mapped points 113 with the representation 12 of the joint 120 at a flexion angle of approximately 30 degrees. FIG. 12 shows the mapped points 113 with the representation 12 of the joint 120 at a flexion angle of approximately 135 degrees.

FIG. 13 shows the representations 10, 11 of FIG. 11, the first implant model 30 that has been associated with the representation 11, and a second implant model 20 that has been associated with the representation 10. In some embodiments, the second implant model 20 may be associated with the representation 10 by aligning the articular surface of the second implant model 20 with at least one of the mapped points 113 as shown in FIG. 13. In this manner, a desired relationship between the implant models 20, 30 may be achieved. As a result, the physical implant components (which correspond to the implant models 20, 30) will have the desired relative placement through some or all of the range of motion of the joint 120 when implanted in the patient's joint 120 by the surgeon.

Figure 14:
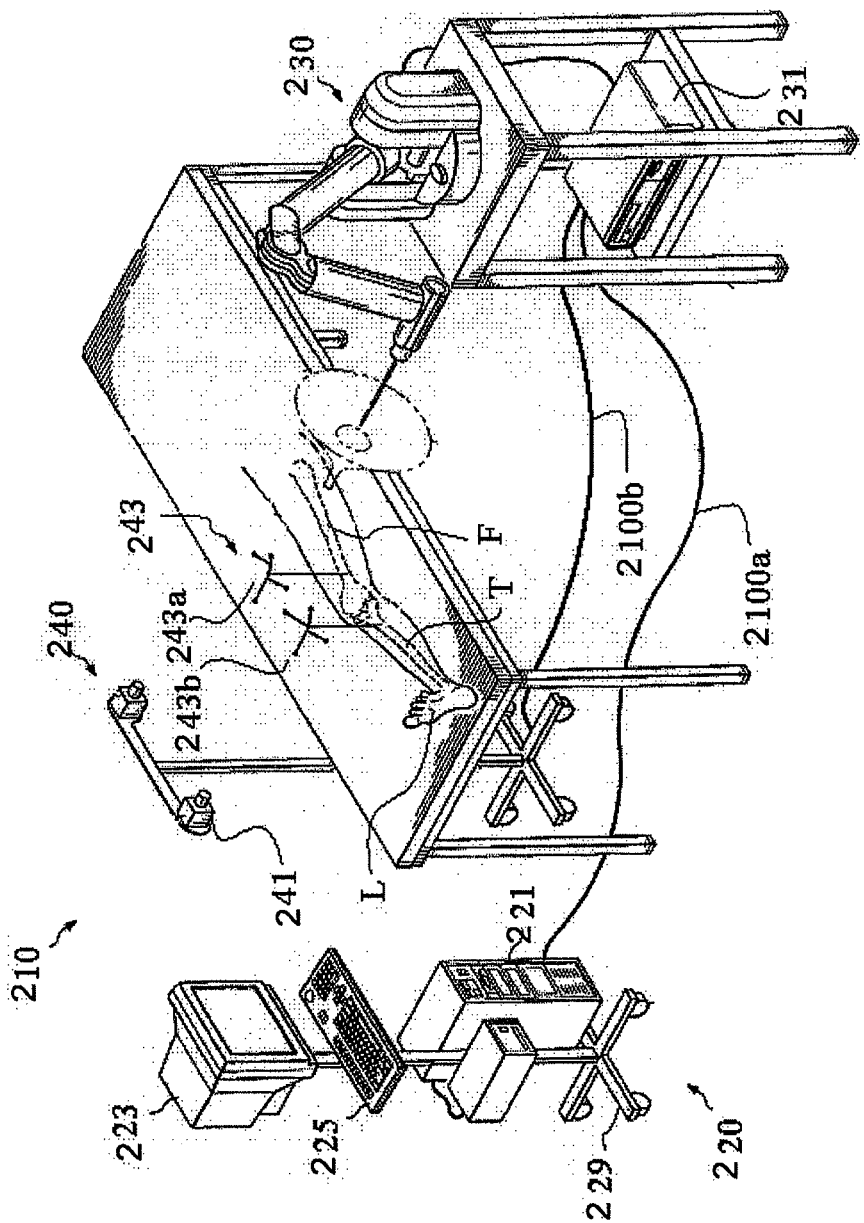
FIG. 14 illustrates an exemplary surgical computer system for implant planning using captured joint motion information.

FIG. 14 shows an embodiment of an exemplary surgical computer system 210 in which the techniques described above can be implemented. Such an exemplary system is described in detail, for example, in U.S. Patent Publication 2006/0142657, published Jun. 29, 2006, which is hereby incorporated by reference herein in its entirety. The surgical system 210 includes a computing system 220, a haptic device 230, and a tracking (or localizing) system 240. In operation, the surgical system 210 enables comprehensive, intraoperative surgical planning. The surgical system 210 also provides haptic guidance to a user (e.g., a surgeon) and/or limits the user's manipulation of the haptic device 230 as the user performs a surgical procedure. Although included for completeness in the illustrated embodiment, the haptic device 230 and its associated hardware and software is not necessary to perform the techniques described herein.

The computing system 220 includes hardware and software for operation and control of the surgical system 210. Such hardware and/or software is configured to enable the system 210 to perform the techniques described herein. In FIG. 14, the computing system 220 includes a computer 221, a display device 223, and an input device 225. The computing system 220 may also include a cart 229.

The computer 221 may be any known computing system but is preferably a programmable, processor-based system. For example, the computer 221 may include a microprocessor, a hard drive, random access memory (RAM), read only memory (ROM), input/output (I/O) circuitry, and any other well-known computer component. The computer 221 is preferably adapted for use with various types of storage devices (persistent and removable), such as, for example, a portable drive, magnetic storage (e.g., a floppy disk), solid state storage (e.g., a flash memory card), optical storage (e.g., a compact disc or CD), and/or network/Internet storage. The computer 221 may comprise one or more computers, including, for example, a personal computer (e.g., an IBM-PC compatible computer) or a workstation (e.g., a SUN or Silicon Graphics workstation) operating under a Windows, MS-DOS, UNIX, or other suitable operating system and preferably includes a graphical user interface (GUI).

The display device 223 is a visual interface between the computing system 220 and the user. The display device 223 is connected to the computer 221 and may be any device suitable for displaying text, images, graphics, and/or other visual output. For example, the display device 223 may include a standard display screen (e.g., LCD, CRT, plasma, etc.), a touch screen, a wearable display (e.g., eyewear such as glasses or goggles), a projection display, a head-mounted display, a holographic display, and/or any other visual output device. The display device 223 may be disposed on or near the computer 221 (e.g., on the cart 229 as shown in FIG. 14) or may be remote from the computer 221 (e.g., mounted on a wall of an operating room or other location suitable for viewing by the user). The display device 223 is preferably adjustable so that the user can position/reposition the display device 223 as needed during a surgical procedure. For example, the display device 223 may be disposed on an adjustable arm (not shown) that is connected to the cart 229 or to any other location well-suited for ease of viewing by the user. The display device 223 may be used to display any information useful for a medical procedure, such as, for example, images of anatomy generated from an image data set obtained using conventional imaging techniques, graphical models (e.g., CAD models of implants, instruments, anatomy, etc.), graphical representations of a tracked object (e.g., anatomy, tools, implants, etc.), digital or video images, registration information, calibration information, patient data, user data, measurement data, software menus, selection buttons, status information, and the like.

In addition to the display device 223, the computing system 220 may include an acoustic device (not shown) for providing audible feedback to the user. The acoustic device is connected to the computer 221 and may be any known device for producing sound. For example, the acoustic device may comprise speakers and a sound card, a motherboard with integrated audio support, and/or an external sound controller. In operation, the acoustic device may be adapted to convey information to the user. For example, the computer 221 may be programmed to signal the acoustic device to produce a sound, such as a voice synthesized verbal indication "DONE," to indicate that a step of a surgical procedure is complete. Similarly, the acoustic device may be used to alert the user to a sensitive condition, such as producing a beep to indicate that a surgical cutting tool is nearing a critical portion of soft tissue.

The input device 225 of the computing system 220 enables the user to communicate with the surgical system 210. The input device 225 is connected to the computer 221 and may include any device enabling a user to provide input to a computer. For example, the input device 225 can be a known input device, such as a keyboard, a mouse, a trackball, a touch screen, a touch pad, voice recognition hardware, dials, switches, buttons, a trackable probe, a foot pedal, a remote control device, a scanner, a camera, a microphone, and/or a joystick.

The computing system 220 is coupled to the computing device 231 via an interface 2100a and to a detection device 241 via an interface 2100b. The interfaces 2100a and 2100b can include a physical interface and a software interface. The physical interface may be any known interface such as, for example, a wired interface (e.g., serial, USB, Ethernet, CAN bus, and/or other cable communication interface) and/or a wireless interface (e.g., wireless Ethernet, wireless serial, infrared, and/or other wireless communication system). The software interface may be resident on the computer 221 and/or the computer 231. In some embodiments, computer 221 and 231 are the same computing device.

The system 210 also includes a tracking (or localizing) system 240 that is configured to determine a pose (i.e., position and orientation) of one or more objects during a surgical procedure to detect movement of the object(s). For example, the tracking system 240 may include a detection device that obtains a pose of an object with respect to a coordinate frame of reference of the detection device. As the object moves in the coordinate frame of reference, the detection device tracks the pose of the object to detect (or enable the surgical system 210 to determine) movement of the object. As a result, the computing system 220 can capture data in response to movement of the tracked object or objects. Tracked objects may include, for example, tools/instruments, patient anatomy, implants/prosthetic devices, and components of the surgical system 210. Using pose data from the tracking system 240, the surgical system 210 is also able to register (or map or associate) coordinates in one space to those in another to achieve spatial alignment or correspondence (e.g., using a coordinate transformation process as is well known). Objects in physical space may be registered to any suitable coordinate system, such as a coordinate system being used by a process running on the computer 221 and/or the computer 231. For example, utilizing pose data from the tracking system 240, the surgical system 210 is able to associate the physical anatomy with a representation of the anatomy (such as an image displayed on the display device 223). Based on tracked object and registration data, the surgical system 210 may determine, for example, a spatial relationship between the image of the anatomy and the relevant anatomy.

Registration may include any known registration technique, such as, for example, image-to-image registration (e.g., monomodal registration where images of the same type or modality, such as fluoroscopic images or MR images, are registered and/or multimodal registration where images of different types or modalities, such as MRI and CT, are registered); image-to-physical space registration (e.g., image-to-patient registration where a digital data set of a patient's anatomy obtained by conventional imaging techniques is registered with the patient's actual anatomy); and/or combined image-to-image and image-to-physical-space registration (e.g., registration of preoperative CT and MRI images to an intraoperative scene). The computer system 210 may also include a coordinate transform process for mapping (or transforming) coordinates in one space to those in another to achieve spatial alignment or correspondence. For example, the surgical system 210 may use the coordinate transform process to map positions of tracked objects (e.g., patient anatomy, etc.) into a coordinate system used by a process running on the computer 231 and/or the computer 221. As is well known, the coordinate transform process may include any suitable transformation technique, such as, for example, rigid-body transformation, non-rigid transformation, affine transformation, and the like.

The tracking system 240 may be any tracking system that enables the surgical system 210 to continually determine (or track) a pose of the relevant anatomy of the patient. For example, the tracking system 240 may comprise a non-mechanical tracking system, a mechanical tracking system, or any combination of non-mechanical and mechanical tracking systems suitable for use in a surgical environment. The non-mechanical tracking system may include an optical (or visual), magnetic, radio, or acoustic tracking system. Such systems typically include a detection device adapted to locate in predefined coordinate space specially recognizable trackable elements (or trackers) that are detectable by the detection device and that are either configured to be attached to the object to be tracked or are an inherent part of the object to be tracked. For example, a trackable element may include an array of markers having a unique geometric arrangement and a known geometric relationship to the tracked object when the trackable element is attached to the tracked object. The known geometric relationship may be, for example, a predefined geometric relationship between the trackable element and an endpoint and axis of the tracked object. Thus, the detection device can recognize a particular tracked object, at least in part, from the geometry of the markers (if unique), an orientation of the axis, and a location of the endpoint within a frame of reference deduced from positions of the markers. The markers may include any known marker, such as, for example, extrinsic markers (or fiducials) and/or intrinsic features of the tracked object. Extrinsic markers are artificial objects that are attached to the patient (e.g., markers affixed to skin, markers implanted in bone, stereotactic frames, etc.) and are designed to be visible to and accurately detectable by the detection device. Intrinsic features are salient and accurately locatable portions of the tracked object that are sufficiently defined and identifiable to function as recognizable markers (e.g., landmarks, outlines of anatomical structure, shapes, colors, or any other sufficiently recognizable visual indicator). The markers may be located using any suitable detection method, such as, for example, optical, electromagnetic, radio, or acoustic methods as are well known. For example, an optical tracking system having a stationary stereo camera pair sensitive to infrared radiation may be used to track markers that emit infrared radiation either actively (such as a light emitting diode or LED) or passively (such as a spherical marker with a surface that reflects infrared radiation). Similarly, a magnetic tracking system may include a stationary field generator that emits a spatially varying magnetic field sensed by small coils integrated into the tracked object.

In one embodiment, as shown in FIG. 14, the tracking system 240 includes a non-mechanical tracking system. In this embodiment, the non-mechanical tracking system is an optical tracking system that comprises a detection device 241 and at least one trackable element (or tracker) configured to be disposed on (or incorporated into) a tracked object and detected by the detection device 241. In FIG. 14, the detection device 41 includes, for example, a stereo camera pair sensitive to infrared radiation and positionable in an operating room where the surgical procedure will be performed. The tracker is configured to be affixed to the tracked object in a secure and stable manner and includes an array of markers (e.g., an array S1 in FIG. 15) having a known geometric relationship to the tracked object. The markers may be active (e.g., light emitting diodes or LEDs) or passive (e.g., reflective spheres, a checkerboard pattern, etc.) and preferably have a unique geometry (e.g., a unique geometric arrangement of the markers) or, in the case of active, wired markers, a unique firing pattern. In operation, the detection device 241 detects positions of the markers, and the unique geometry (or firing pattern) and known geometric relationship to the tracked object enable the surgical system 210 to calculate a pose of the tracked object based on the positions of the markers.

The non-mechanical tracking system may include a trackable element (or tracker) for each object the user desires to track. For example, in one embodiment, the non-mechanical tracking system includes anatomy trackers 243a and 243b, generally 243 (to track patient anatomy).

Figure 15:
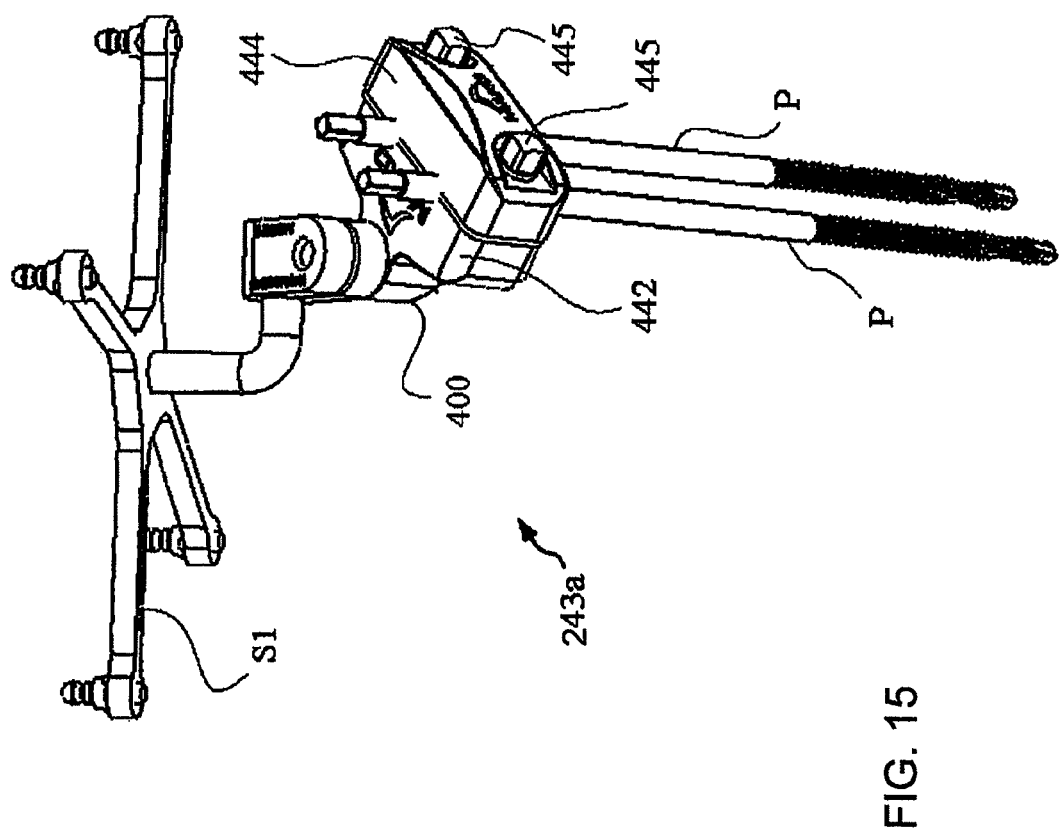
FIG. 15 illustrates an exemplary tracker used by the surgical computer system for implant planning using captured joint motion information.

In FIG. 14, the anatomy tracker 243 is disposed on a relevant portion of a patient's anatomy (such as a bone) and is adapted to enable the relevant anatomy to be tracked by the detection device 241. The anatomy tracker 243 includes a fixation device for attachment to the anatomy. The fixation device may be, for example, a bone pin, surgical staple, screw, clamp, wearable device, intramedullary rod, or the like. In one embodiment, the anatomy tracker 243 is configured for use during knee replacement surgery to track a femur F and a tibia T of a patient. In this embodiment, as shown in FIG. 14, the anatomy tracker 243 includes a first tracker 243a adapted to be disposed on the femur F and a second tracker 243b adapted to be disposed on the tibia T. FIG. 15 illustrates the first tracker 243a, which includes a fixation device comprising bone pins P and a unique array S1 of markers (e.g., reflective spheres). The array S1 is affixed to a connection mechanism 400 that is adapted to be removably secured to both of the bone pins P. For example, as shown in FIG. 15, the connection mechanism 400 may include a first portion 442, a second portion 444, and screws 445. To install the first tracker 43a on the femur F, the user screws the bone pins P into the femur F, slides the connection mechanism 400 over the bone pins P, and tightens the screws 445 to draw the first and second portions 442 and 444 together to thereby securely fix the connection mechanism 400 to the bone pins P. Once secured, the connection mechanism 400 imparts additional stability to the bone pins P. The second tracker 243b is identical to the first tracker 243a except the second tracker 243b is installed on the tibia T and has its own unique array of markers. When installed on the patient, the first and second trackers 243a and 243b enable the detection device 241 to track motion of the femur F and the tibia T during knee replacement surgery. As a result, the surgical system 210 is able to detect and capture bone motion in real-time as an individual moves his or her joint through its range of motion.

Figure 16:
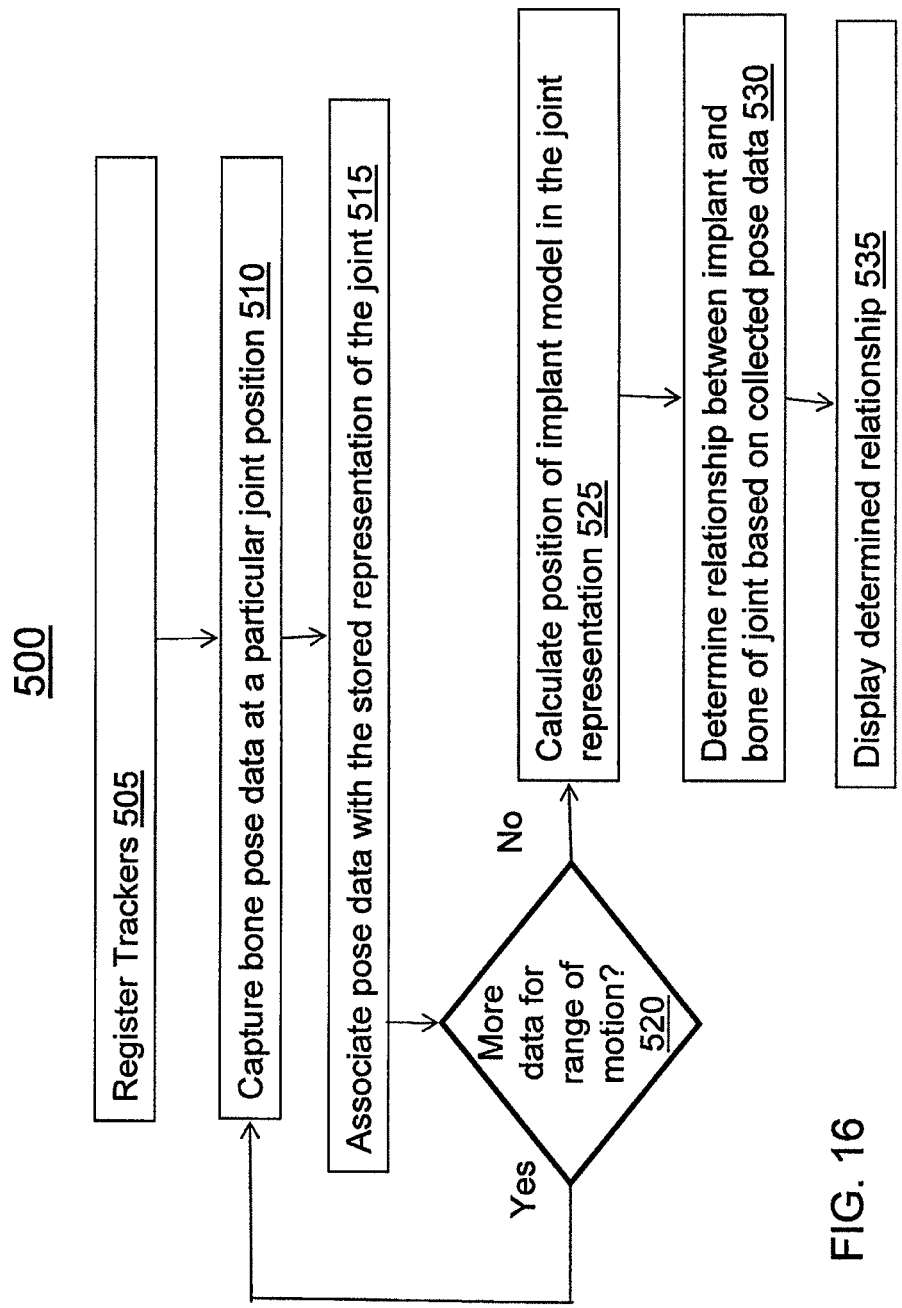
FIG. 16 illustrates an exemplary method for implant planning using captured joint motion information.

FIG. 16 illustrates an exemplary process 500 for implant planning using captured joint motion information. In describing the process 500, the exemplary system 210 of FIG. 14 will be used. In FIG. 14, trackers 243a and 243b are inserted into the femur F and tibia T, respectively. After these trackers are securely attached to the bones of the knee joint, the trackers are registered (505) using tracking system 240 and computing system 220. Once registered, the computing system 220 captures (510) pose data of the femur relative to tibia at a particular angle, for example zero degrees (e.g., full extension). Capturing data refers to storing the data, at least on a temporary basis. Capturing can also refer to the detection of the pose data, for example, through the use of trackers and a detection device, and the transmission of that data to its storage location or some processing device that uses the data. Although pose data (position and orientation) is captured in the process 500, it is not necessary to use pose data in all embodiments. For example, some embodiments, including embodiments using system 210, can use less than all of the pose data, for example only position data, to implement the techniques described herein.

In the process 500, for example using the transform process as described above, the computing system 220 associates (515) the pose data with the one or more stored representations of the bones of the joint. These representations can include images and/or models of the bones, such as segmented CT data, that have been generated for the particular individual for which the bone pose data is being captured (510).

The computing system 220 determines (520) whether any more data is needed for the range of motion. This can be automated, for example by having a set of predetermined angles at which data is collected. If data has not been taken at each of the predetermined angles, the computing system 220 determines (520) that additional data is needed and displays or otherwise communicates to the operator the next angle to which the joint should be positioned. Upon indication by the operator that the joint is at the indicated position, the computing system 220 communicates with the tracking system 240 to retrieve the pose of the trackers and repeats steps 510 and 515. In addition or as an alternative to the set of predetermined angles, the computing system 220 can, through an interface (e.g., displayed text, voice synthesis, etc.), ask the operator whether there are any additional angles at which data should be taken. Typically, there are at least two angles at which data is captured to calculate the relative positions of the bones through a range of motion of the joint.

If there are no more angles at which data needs to be captured, the computing system 220 can calculate (525) the position of the implant model in the joint representation. Such a calculation can take into account input from the user. More specifically, the user of system 220 can, for example through the use of a GUI, manipulate the placement of the implant within the joint representation. Using the implant position and the captured pose data, or some derivative thereof, the computing system 220 can determine (530) the relationship (e.g., a physical distance) between the implant boundaries and the boundaries of a bone of the joint with which the implant will interact. The computer system 220 displays (535) the determined relationship. As described above, there are many ways in which the determined relationship can be displayed, such as a measurement, a graph of the measurement at some or all joint angles, a visual representation of the implant and joint, and mapped points.

The above-described techniques can be implemented in digital electronic circuitry, or in computer hardware, firmware, software, or in combinations of them. The implementation can be as a computer program product, i.e., a computer program tangibly embodied in an information carrier, e.g., in a machine-readable storage device, for execution by, or to control the operation of, data processing apparatus, e.g., a programmable processor, a computer, or multiple computers. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps can be performed by one or more programmable processors executing a computer program to perform functions of the invention by operating on input data and generating output. Method steps can also be performed by, and apparatus can be implemented as, special purpose logic circuitry, e.g., an FPGA (field programmable gate array) or an ASIC (application-specific integrated circuit). Modules can refer to portions of the computer program and/or the processor/special circuitry that implements that functionality.

The above described techniques can be implemented in a distributed computing system that includes a back-end component, e.g., as a data server, and/or a middleware component, e.g., an application server, and/or a front-end component, e.g., a client computer having a graphical user interface and/or a Web browser through which a user can interact with an example implementation, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the Internet, and include both wired and wireless networks.

The computing system can include clients and servers. A client and server are generally remote from each other and typically interact through a communication network. The relationship of client and server arises by virtue of computer programs running on the respective computers and having a client-server relationship to each other.

Comprise, include, have and/or plural forms of each are open ended and include the listed parts and can include additional parts that are not listed. And/or is also open ended and includes one or more of the listed parts and combinations of the listed parts.

The invention has been described in terms of particular embodiments. The alternatives described herein are examples for illustration only and not to limit the alternatives in any way. The steps of the invention can be performed in a different order and still achieve desirable results. Other embodiments are within the scope of the following claims.

What is claimed is:

1. A surgical planning method comprising:
capturing data, using a tracking system associated with a computing system as a native joint is moved within, a range of motion of a joint the joint comprising a first bone and a second bone;
wherein the computing system is further used to perform the steps of:
representing the first bone of the joint;
associating a first implant model with the representation of the first bone;
representing a second bone of the joint;
associating a second implant model with the representation of the second bone;
based on the captured data, determining a distance from at least one point on a surface of the first implant model to at least one point on a surface of the second implant model at a plurality of angles within the range of motion of the joint, and
displaying information representative of the respective determined distances at the plurality of angles, wherein the information representative of the respective determined distances at the plurality of angles is displayed in the form of a bar chart indicating at least one of the plurality of angles and the respective determined distance for the at least one of the plurality of angles.

2. The method of claim 1, further comprising enabling a user to change a position of the first implant model.

3. The method of claim 2, further comprising:
associating the first implant model with the representation of the first bone based on the changed position; and
based on the captured data, determining a relationship between at least one point on the surface the first implant model at its changed position and at least one point on the surface on the second implant model through at least a portion of the range of motion of the joint.

4. The method of claim 1, wherein capturing comprises:
tracking a position of the first bone and a position of the second bone; and
recording the positions as the joint moves through the range of motion.

5. The method of claim 1, further comprising:
representing a position of the first implant model relative to a position of the second implant model; and comparing the positions at any selected angle within the range of motion of the joint, inclusive.

6. The method of claim 1, wherein determining distances comprises identifying an overlap, a gap, or both between the first implant model and the second implant model associated with the second bone at one or more angles within the range of motion of the joint.

7. The method of claim 6, wherein displaying comprises displaying a calculated measurement of the overlap, the gap, or both at any selected angle or at a plurality of angles within the range of motion of the joint.

8. The method of claim 6, wherein displaying comprises displaying of the overlap, the gap, or both in a representation of at least a portion of the joint at one or more angles within the range of motion of the joint.

9. The method of claim 1, wherein capturing further comprises capturing data representative of a manipulation of the joint to achieve a desired internal/external angle, varus/valgus angle, flexion angle, or any combination thereof.

10. The method of claim 9, further comprising enabling a user to manipulate placement of at least one implant model corresponding to at least a portion of an actual implant so that the determined relationship through at least a portion of the range of motion of the joint allows the desired internal/external angle, varus/valgus angle, flexion angle, or any combination thereof.

11. A non-transitory computer-readable medium tangibly embodied in an information carrier, including instructions being operable to cause a data processing apparatus to:
capture data as a native joint is moved within a range of motion of a joint, the joint comprising a first bone and a second bone;
represent the first bone of the joint;
associate a first implant model with the representation of the first bone;
represent the second bone of the joint;
associate a second implant model with the representation of the second bone;
determine a distance from at least one point on a surface of the first implant model to at least one point on a surface of the second implant model at a plurality of angles within the range of motion of the joint;
display information representative of the respective determined distances at the plurality of angles, wherein the information representative of the respective determined distances at the plurality of angles is displayed in the form of a bar chart indicating at least one of the plurality of angles and the respective determined distance for the at least one of the plurality of angles.

12. A surgical planning method, comprising the steps of:
capturing data, using a tracking system associated with a computing system, as a native joint is moved within a range of motion of a joint, the joint comprising a first bone and a second bone;
wherein the computing system is further used to perform the steps of:
creating a representation of the joint comprising a representation of the first bone and a representation of the second bone;
superimposing a first implant model on the representation of the first bone and a second implant model on the representation of the second bone;
based on the captured data, determining a distance from at least one point on a surface of the first implant model to at least one point on a surface of the second implant model at a plurality of angles within the range of motion of the joint;
displaying information representative of the respective determined distances at the plurality of angles, wherein the information representative of the respective determined distances at the plurality of angles is displayed in the form of a bar chart indicating at least one of the plurality of angles and the respective determined distance for the at least one of the plurality of angles; and
adjusting a size, a shape, a position, or any combination thereof of the first implant model, the second implant model, or both based on the determined relationship.

13. A surgical computing system comprising a computer configured to:
capture data as a native joint is moved within a range of motion of a joint;
represent a first bone of the joint;
associate a first implant model with the representation of the first bone;
represent a second bone of the joint;
associate a second implant model with the representation of the second bone;
based on the captured data, determine a distance from at least one point on a surface of the first implant model to at least one point on a surface of the second implant model at a plurality of angles within the range of motion of the joint;
display information representative of the respective determined distances at the plurality of angles, wherein the information representative of the respective determined distances at the plurality of angles is displayed in the form of a bar chart indicating at least one of the plurality of angles and the respective determined distance for the at least one of the plurality of angles.

14. The surgical computing system of claim 13 further comprising a tracking system in communication with the computer, the tracking system including a detection device and one or more trackers which each include a coupling means to couple the tracker to a bone of the joint.

15. The surgical computing system of claim 13 further comprising a display in communication with the computer and configured to display information received from the computer that is representative of the determined distances.

16. The surgical computing system of claim 13 wherein the computer is further configured to generate a user interface that enables a user to select an angle at which the determined distances are calculated, displayed, or both.

17. The surgical computing system of claim 13 wherein the computer is further configured to generate a user interface that enables a user to change a position of the first implant model and to update the determined distances based on the changed position of the first implant model.

18. The method of claim 2, further comprising updating the determined distances based on the changed position of the first implant model.

19. A surgical planning method comprising:
capturing data, using a tracking system associated with a computing system, as a native joint is moved within a range of motion the joint comprising a first bone and a second bone;
wherein the computing system is further used to perform the steps of:
associating a first implant model with a representation of the first bone;
associating a second implant model with a representation of the second bone;
based on the captured data, determining a distance between at least one point on a surface of the first implant model and one of (1) at least one point on a surface of the representation of the second bone or (2) at least one point on a surface of the second implant model associated with the representation of the second bone at a plurality of angles within the range of motion of the joint; and displaying information representative of the respective determined distances at the plurality of angles, wherein the information representative of the respective determined distances at the plurality of angles is displayed in the form of a bar chart indicating at least one of the plurality of angles and the respective determined distance for the at least one of the plurality of angles.

20. The method of claim 19, wherein displaying comprises displaying the representation of the first bone, the representation of the second bone, or both.

21. The method of claim 19, wherein displaying comprises displaying the first implant model, the second implant model, or both.

22. The method of claim 1, wherein the bar chart comprises a horizontal axis representing the at least one of the plurality of angles and a vertical axis representing the determined distance between the at least one point on the surface of the first implant model and the at least one point on the surface of the second implant model.

23. The method of claim 1, further comprising:
adjusting a size, a shape, a position, or any combination thereof of the first implant model, the second implant model, or both based on the determined relationship; and
updating the display of the respective determined distances based on the adjusted first implant model, second implant model, or both.

* * * * *